US012611326B2

(12) United States Patent
Ivri

(10) Patent No.: US 12,611,326 B2
(45) Date of Patent: *Apr. 28, 2026

(54) HYDRODYNAMICALLY ACTUATED PRESERVATIVE FREE DISPENSING SYSTEM HAVING A COLLAPSIBLE LIQUID RESERVOIR

(71) Applicant: Bausch + Lomb Ireland Limited, Dublin (IE)

(72) Inventor: Yehuda Ivri, Newport Coast, CA (US)

(73) Assignee: Bausch + Lomb Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/653,727

(22) Filed: May 2, 2024

(65) Prior Publication Data

US 2024/0277516 A1 Aug. 22, 2024

Related U.S. Application Data

(63) Continuation of application No. 17/233,135, filed on Apr. 16, 2021, now Pat. No. 12,090,087.

(Continued)

(51) Int. Cl.
*A61F 9/00* (2006.01)
*A61J 1/14* (2023.01)

(52) U.S. Cl.
CPC ........... *A61F 9/0008* (2013.01); *A61J 1/1443* (2013.01)

(58) Field of Classification Search
CPC ... A61F 9/0008; A61F 9/0026; A61M 11/006; A61M 11/008
See application file for complete search history.

(56) References Cited

U.S. PATENT DOCUMENTS 3,598,121 A 8/1971 John
3,640,274 A 2/1972 Costello
(Continued)

FOREIGN PATENT DOCUMENTS

CN 103118642 A 5/2013
CN 104146816 A 11/2014
(Continued)

OTHER PUBLICATIONS

Abidi et al., "Lifilegrast: A Novel Drug for Treatment of Dry Eye Disease", Journal of Pharmacology and Pharmacotherapy, 2016, vol. 7, pp. 194-198.
(Continued)

*Primary Examiner* — Philip R Wiest
*Assistant Examiner* — Arjuna P Chatrathi
(74) *Attorney, Agent, or Firm* — Perilla Knox Hildebrandt Staley & Amy LLP; Stephanie Davy-Jow; Bradley K. Groff

(57) ABSTRACT

Multi-dose preservative-free ocular fluid delivery devices are provided. The fluid delivery device includes a fluid dispensing system and a fluid package for storing a liquid therein and supplying said liquid to the dispensing system. The dispensing system comprises an elongated chamber which includes a check valve which defines a frontal closure to the chamber. The valve is normally closed and hermetically seals the chamber. The dispenser includes a vibration motor that induces oscillations to the chamber and to the fluid within. The oscillations of the chamber impart momentum to the fluid stored in the chamber which in turn imparts force that cyclically opens the valve to dispense streams or liquid droplets. Fluid is dispensed only when the motor oscillates while otherwise the valve is hermetically closed. The fluid package can be made collapsible to remove the need to vent it.

18 Claims, 8 Drawing Sheets

Related U.S. Application Data

(60) Provisional application No. 63/166,754, filed on Mar. 26, 2021, provisional application No. 63/011,808, filed on Apr. 17, 2020.

(56) References Cited

U.S. PATENT DOCUMENTS

| | | | |
|---|---|---|---|
| 3,779,245 A | 12/1973 | Windsor | |
| 3,812,854 A | 5/1974 | Michaels et al. | |
| 3,861,386 A | 1/1975 | Harris et al. | |
| 3,934,585 A | 1/1976 | Maurice | |
| 3,951,310 A * | 4/1976 | Steiman | B65D 83/7714 |
| | | | 222/340 |
| 3,970,250 A | 7/1976 | Drews | |
| 3,976,072 A | 8/1976 | Walker | |
| 4,159,803 A | 7/1979 | Cameto et al. | |
| 4,300,546 A | 11/1981 | Kruber | |
| 4,334,531 A | 6/1982 | Reichl et al. | |
| 4,338,576 A | 7/1982 | Takahashi et al. | |
| 4,344,744 A | 8/1982 | Schuster et al. | |
| 4,352,459 A | 10/1982 | Berger et al. | |
| 4,465,234 A | 8/1984 | Maehara et al. | |
| 4,632,311 A | 12/1986 | Nakane et al. | |
| 4,655,393 A | 4/1987 | Berger | |
| 4,793,339 A | 12/1988 | Matsumoto et al. | |
| 4,850,534 A | 7/1989 | Takahashi et al. | |
| 4,882,150 A | 11/1989 | Kaufman | |
| 4,952,581 A | 8/1990 | Bito et al. | |
| 4,961,345 A | 10/1990 | Tsuruoka et al. | |
| 4,976,259 A | 12/1990 | Higson et al. | |
| 4,981,625 A | 1/1991 | Rhim et al. | |
| 5,025,957 A | 6/1991 | Ranalletta et al. | |
| 5,171,306 A | 12/1992 | Vo | |
| 5,232,363 A | 8/1993 | Meller | |
| 5,368,582 A | 11/1994 | Bertera | |
| 5,370,317 A | 12/1994 | Weston | |
| 5,487,378 A | 1/1996 | Robertson et al. | |
| 5,549,249 A | 8/1996 | Foster et al. | |
| 5,624,057 A | 4/1997 | Lifshey | |
| 5,627,611 A | 5/1997 | Scheiner | |
| 5,630,793 A | 5/1997 | Rowe | |
| 5,657,926 A | 8/1997 | Toda | |
| 5,692,651 A | 12/1997 | Fuchs | |
| 5,811,443 A | 9/1998 | DeSantis, Jr. et al. | |
| 5,828,394 A | 10/1998 | Khuri-Yakub et al. | |
| 5,938,117 A | 8/1999 | Ivri | |
| 5,958,342 A | 9/1999 | Gamble et al. | |
| 5,960,224 A | 9/1999 | Sanada et al. | |
| 6,024,717 A | 2/2000 | Ball et al. | |
| 6,062,212 A | 5/2000 | Davison et al. | |
| 6,065,623 A | 5/2000 | Hierzer et al. | |
| 6,095,376 A | 8/2000 | Hennemann et al. | |
| 6,196,218 B1 | 3/2001 | Voges | |
| 6,232,129 B1 | 5/2001 | Wiktor | |
| 6,273,092 B1 | 8/2001 | Nolan | |
| 6,302,101 B1 * | 10/2001 | Py | B05B 11/1066 |
| | | | 128/200.22 |
| 6,467,476 B1 | 10/2002 | Ivri et al. | |
| RE38,077 E | 4/2003 | Cohen et al. | |
| 6,543,442 B2 | 4/2003 | Gonda et al. | |
| 6,629,646 B1 | 10/2003 | Ivri | |
| 6,730,066 B1 | 5/2004 | Bennwik et al. | |
| 6,758,837 B2 | 7/2004 | Peclat et al. | |
| 6,869,275 B2 | 3/2005 | Dante et al. | |
| 7,066,398 B2 | 6/2006 | Borland et al. | |
| 7,105,357 B1 | 9/2006 | Kalkum et al. | |
| 7,201,732 B2 | 4/2007 | Anderson et al. | |
| 7,314,938 B2 | 1/2008 | Shen et al. | |
| 7,571,722 B2 | 8/2009 | Wuttke et al. | |
| 7,745,460 B2 | 6/2010 | Shen et al. | |
| 7,790,743 B2 | 9/2010 | Shen et al. | |
| 7,874,467 B2 | 1/2011 | Pardes et al. | |
| 7,883,031 B2 | 2/2011 | Collins, Jr. et al. | |
| 7,928,122 B2 | 4/2011 | Shen et al. | |
| 8,012,136 B2 | 9/2011 | Collins, Jr. et al. | |
| 8,048,047 B2 | 11/2011 | Domash | |
| 8,056,766 B2 | 11/2011 | Grevin | |
| 8,128,606 B2 | 3/2012 | Anderson et al. | |
| 8,133,210 B2 | 3/2012 | Al-Abdulla et al. | |
| 8,144,399 B2 | 3/2012 | Steenblik et al. | |
| 8,168,655 B2 | 5/2012 | Gadek et al. | |
| 8,273,307 B2 | 9/2012 | Eickhoff et al. | |
| 8,367,701 B2 | 2/2013 | Burnier et al. | |
| 8,398,001 B2 | 3/2013 | Borland et al. | |
| 8,435,544 B2 | 5/2013 | Mitra et al. | |
| 8,544,462 B2 | 10/2013 | Papania et al. | |
| 8,545,463 B2 | 10/2013 | Collins, Jr. et al. | |
| 8,592,450 B2 | 11/2013 | Gadek et al. | |
| 8,629,111 B2 | 1/2014 | Acheampong et al. | |
| 8,633,162 B2 | 1/2014 | Acheampong et al. | |
| 8,642,556 B2 | 2/2014 | Acheampong et al. | |
| 8,648,048 B2 | 2/2014 | Acheampong et al. | |
| 8,684,980 B2 | 4/2014 | Hunter et al. | |
| 8,685,930 B2 | 4/2014 | Acheampong et al. | |
| 8,722,728 B2 | 5/2014 | Wong et al. | |
| 8,733,935 B2 | 5/2014 | Ballou, Jr. et al. | |
| 8,863,998 B2 | 10/2014 | Painchaud et al. | |
| 8,927,574 B2 | 1/2015 | Burnier | |
| 8,927,921 B1 | 1/2015 | Nelms et al. | |
| 8,936,021 B2 | 1/2015 | Collins, Jr. | |
| 9,039,666 B2 | 5/2015 | Voss et al. | |
| 9,068,566 B2 | 6/2015 | Ivri | |
| 9,085,553 B2 | 7/2015 | Zeller et al. | |
| 9,087,145 B2 | 7/2015 | Ballou, Jr. et al. | |
| 9,186,690 B2 | 11/2015 | Scanlon et al. | |
| 9,216,174 B2 | 12/2015 | Shen et al. | |
| 9,238,532 B2 | 1/2016 | Decock et al. | |
| 9,248,191 B2 | 2/2016 | Acheampong et al. | |
| 9,353,088 B2 | 5/2016 | Burnier | |
| 9,447,077 B2 | 9/2016 | Burnier et al. | |
| 9,597,230 B2 | 3/2017 | Haffner et al. | |
| 9,676,525 B2 | 6/2017 | Greiner-Perth et al. | |
| 9,700,686 B2 | 7/2017 | Gavini et al. | |
| 9,801,757 B2 | 10/2017 | Voss et al. | |
| 9,808,825 B2 | 11/2017 | Aguilar et al. | |
| 9,867,933 B2 | 1/2018 | Pardes et al. | |
| 9,890,141 B2 | 2/2018 | Burnier | |
| 10,073,949 B2 | 9/2018 | Ballou, Jr. et al. | |
| 10,105,720 B2 | 10/2018 | Decock et al. | |
| 10,124,000 B2 | 11/2018 | Shen et al. | |
| 10,154,923 B2 | 12/2018 | Hunter et al. | |
| 10,174,017 B2 | 1/2019 | deLong et al. | |
| 10,314,740 B2 | 6/2019 | Kraft | |
| 10,624,781 B2 | 4/2020 | Ivri | |
| 11,278,448 B2 | 3/2022 | Palanker et al. | |
| 12,090,087 B2 * | 9/2024 | Ivri | A61J 1/1443 |
| 2001/0035184 A1 | 11/2001 | Schuler et al. | |
| 2001/0036424 A1 | 11/2001 | Takahashi et al. | |
| 2001/0036449 A1 | 11/2001 | Garst | |
| 2002/0078947 A1 | 6/2002 | Gumaste | |
| 2002/0124843 A1 | 9/2002 | Skiba et al. | |
| 2002/0158196 A1 | 10/2002 | Berggren et al. | |
| 2002/0161344 A1 | 10/2002 | Peclat et al. | |
| 2002/0185125 A1 | 12/2002 | Klimowicz et al. | |
| 2002/0190079 A1 | 12/2002 | Hamamoto | |
| 2003/0052573 A1 | 3/2003 | Wischnewskiy | |
| 2003/0065294 A1 | 4/2003 | Pickup et al. | |
| 2003/0071071 A1 | 4/2003 | Garcia et al. | |
| 2003/0140921 A1 | 7/2003 | Smith et al. | |
| 2004/0039355 A1 | 2/2004 | Gonzalez et al. | |
| 2004/0050861 A1 | 3/2004 | Lisec et al. | |
| 2004/0138630 A1 | 7/2004 | Al-Abdulla et al. | |
| 2004/0163645 A1 | 8/2004 | Connelly et al. | |
| 2004/0173642 A1 | 9/2004 | Clifford et al. | |
| 2004/0204674 A1 | 10/2004 | Anderson et al. | |
| 2004/0215157 A1 | 10/2004 | Peclat et al. | |
| 2004/0256487 A1 | 12/2004 | Collins, Jr. et al. | |
| 2004/0263567 A1 | 12/2004 | Hess et al. | |
| 2005/0001981 A1 | 1/2005 | Anderson et al. | |
| 2005/0006417 A1 | 1/2005 | Nicol et al. | |
| 2005/0107832 A1 | 5/2005 | Bernabei | |
| 2005/0172962 A1 | 8/2005 | Gumaste et al. | |
| 2005/0207917 A1 | 9/2005 | Koerner et al. | |

(56)                    References Cited

U.S. PATENT DOCUMENTS

| | | | |
|---|---|---|---|
| 2005/0240162 A1* | 10/2005 | Chen | A61F 9/0008 |
| | | | 604/298 |
| 2005/0261641 A1 | 11/2005 | Warchol et al. | |
| 2006/0065677 A1 | 3/2006 | Py et al. | |
| 2006/0069358 A1 | 3/2006 | Gerondale | |
| 2006/0147313 A1 | 7/2006 | Zengerle et al. | |
| 2006/0210604 A1 | 9/2006 | Dadey et al. | |
| 2007/0051362 A1 | 3/2007 | Sullivan et al. | |
| 2007/0088267 A1 | 4/2007 | Shekalim | |
| 2007/0088268 A1 | 4/2007 | Edwards | |
| 2007/0102455 A1 | 5/2007 | Stark et al. | |
| 2007/0119969 A1 | 5/2007 | Collins et al. | |
| 2007/0195151 A1 | 8/2007 | Anderson et al. | |
| 2007/0268340 A1 | 11/2007 | Dacquay et al. | |
| 2007/0295332 A1 | 12/2007 | Ziegler et al. | |
| 2008/0039807 A1 | 2/2008 | Pine | |
| 2008/0202514 A1 | 8/2008 | Kriksunov et al. | |
| 2008/0214940 A1 | 9/2008 | Benaron et al. | |
| 2008/0233053 A1 | 9/2008 | Gross et al. | |
| 2008/0247264 A1 | 10/2008 | Gabl et al. | |
| 2008/0257911 A1 | 10/2008 | Choi et al. | |
| 2009/0060793 A1 | 3/2009 | Eickhoff et al. | |
| 2009/0114742 A1 | 5/2009 | Collins, Jr. | |
| 2009/0134235 A1 | 5/2009 | Ivri | |
| 2009/0182291 A1 | 7/2009 | Eilat | |
| 2009/0192443 A1 | 7/2009 | Collins, Jr. | |
| 2009/0212127 A1 | 8/2009 | Reynolds et al. | |
| 2009/0212133 A1 | 8/2009 | Collins, Jr. | |
| 2009/0223513 A1 | 9/2009 | Papania et al. | |
| 2009/0236374 A1* | 9/2009 | Pardes | B05B 11/1032 |
| | | | 222/494 |
| 2010/0001090 A1 | 1/2010 | Neergaard et al. | |
| 2010/0005903 A1 | 1/2010 | Beavis | |
| 2010/0013352 A1 | 1/2010 | Pletner et al. | |
| 2010/0044460 A1 | 2/2010 | Sauzade | |
| 2010/0072301 A1* | 3/2010 | Cater | F16K 31/0655 |
| | | | 239/333 |
| 2010/0072302 A1 | 3/2010 | Cater | |
| 2010/0076388 A1 | 3/2010 | Cater | |
| 2010/0186738 A1 | 7/2010 | Kobayashi et al. | |
| 2010/0222752 A1 | 9/2010 | Collins, Jr. et al. | |
| 2010/0236545 A1 | 9/2010 | Kern | |
| 2010/0295420 A1 | 11/2010 | Wierach | |
| 2010/0326431 A1 | 12/2010 | Yu | |
| 2011/0074247 A1 | 3/2011 | Hohlfeld et al. | |
| 2011/0102735 A1 | 5/2011 | Gupta et al. | |
| 2011/0106025 A1 | 5/2011 | Hall et al. | |
| 2011/0146670 A1 | 6/2011 | Gallem et al. | |
| 2011/0284579 A1 | 11/2011 | Pardes et al. | |
| 2011/0293452 A1 | 12/2011 | Kim et al. | |
| 2011/0305425 A1 | 12/2011 | Fabrykowski et al. | |
| 2012/0017898 A1 | 1/2012 | Moller | |
| 2012/0062840 A1 | 3/2012 | Ballou, Jr. et al. | |
| 2012/0070467 A1 | 3/2012 | Ballou, Jr. et al. | |
| 2012/0143152 A1 | 6/2012 | Hunter et al. | |
| 2012/0179122 A1 | 7/2012 | Eilat et al. | |
| 2012/0197219 A1 | 8/2012 | Scanlon et al. | |
| 2012/0304929 A1 | 12/2012 | Ivri | |
| 2013/0002095 A1 | 1/2013 | Van Der Linden | |
| 2013/0017283 A1 | 1/2013 | Zemel et al. | |
| 2013/0025038 A1 | 1/2013 | Frey et al. | |
| 2013/0053042 A1 | 2/2013 | Tanikawa et al. | |
| 2013/0079733 A1 | 3/2013 | Burt et al. | |
| 2013/0118619 A1 | 5/2013 | Loth et al. | |
| 2013/0140225 A1 | 6/2013 | Decock et al. | |
| 2013/0150812 A1 | 6/2013 | Hunter et al. | |
| 2013/0152796 A1 | 6/2013 | Pawl | |
| 2013/0153677 A1 | 6/2013 | Leen et al. | |
| 2013/0164436 A1 | 6/2013 | Yagi et al. | |
| 2013/0172830 A1 | 7/2013 | Hunter et al. | |
| 2013/0206857 A1 | 8/2013 | Ivri | |
| 2013/0299607 A1 | 11/2013 | Wilkerson et al. | |
| 2013/0345672 A1 | 12/2013 | Ferreri et al. | |
| 2014/0088524 A1 | 3/2014 | Marx | |
| 2014/0113946 A1 | 4/2014 | Abad | |
| 2014/0157956 A1 | 6/2014 | Date et al. | |
| 2014/0171490 A1 | 6/2014 | Gross et al. | |
| 2014/0187969 A1* | 7/2014 | Hunter | A61B 3/14 |
| | | | 604/521 |
| 2014/0214024 A1 | 7/2014 | Eichler | |
| 2014/0224267 A1 | 8/2014 | Levitz et al. | |
| 2014/0242022 A1 | 8/2014 | Vehige et al. | |
| 2014/0249491 A1 | 9/2014 | Ballou, Jr. et al. | |
| 2014/0257172 A1 | 9/2014 | Yalamanchili | |
| 2014/0274910 A1 | 9/2014 | Cumberlidge et al. | |
| 2014/0276054 A1 | 9/2014 | Hossack et al. | |
| 2014/0285121 A1 | 9/2014 | Balogh et al. | |
| 2014/0323931 A1* | 10/2014 | Avni | A61M 11/00 |
| | | | 601/46 |
| 2014/0336596 A1 | 11/2014 | Wochele | |
| 2014/0336618 A1 | 11/2014 | Wilkerson et al. | |
| 2015/0018781 A1 | 1/2015 | Rinderknect et al. | |
| 2015/0035180 A1 | 2/2015 | Shen et al. | |
| 2015/0036219 A1 | 2/2015 | Shen et al. | |
| 2015/0040891 A1* | 2/2015 | Avni | A61M 15/003 |
| | | | 128/200.14 |
| 2015/0086397 A1 | 3/2015 | Ma | |
| 2015/0097050 A1 | 4/2015 | Ciervo | |
| 2015/0139973 A1 | 5/2015 | Steinfeld et al. | |
| 2015/0144128 A1 | 5/2015 | Hijlkema et al. | |
| 2015/0209174 A1 | 7/2015 | Abreu | |
| 2015/0209178 A1 | 7/2015 | Blakey et al. | |
| 2015/0238689 A1 | 8/2015 | Shimizu | |
| 2015/0256730 A1 | 9/2015 | Shen et al. | |
| 2015/0276994 A1 | 10/2015 | Shen et al. | |
| 2015/0308421 A1 | 10/2015 | Vogt | |
| 2015/0328151 A1 | 11/2015 | Ballou, Jr. et al. | |
| 2015/0352297 A1 | 12/2015 | Stedman et al. | |
| 2016/0107180 A1 | 4/2016 | Decock et al. | |
| 2016/0120833 A1 | 5/2016 | Wan et al. | |
| 2016/0129467 A1 | 5/2016 | Ciardella et al. | |
| 2016/0199225 A1 | 7/2016 | Ivri | |
| 2016/0199230 A1 | 7/2016 | Doshi et al. | |
| 2016/0213866 A1 | 7/2016 | Tan | |
| 2016/0263314 A1 | 9/2016 | Pardes et al. | |
| 2016/0296367 A1 | 10/2016 | Ivri | |
| 2016/0354559 A1 | 12/2016 | Gavini et al. | |
| 2017/0028626 A1 | 2/2017 | Delrot et al. | |
| 2017/0136484 A1 | 5/2017 | Wilkerson et al. | |
| 2017/0138357 A1 | 5/2017 | Kondo et al. | |
| 2017/0151088 A1 | 6/2017 | Ballou, Jr. et al. | |
| 2017/0156927 A1 | 6/2017 | Richter et al. | |
| 2017/0182510 A1 | 6/2017 | Wilkerson et al. | |
| 2017/0187969 A1 | 6/2017 | Kitamori et al. | |
| 2017/0274159 A1 | 9/2017 | Gavini et al. | |
| 2017/0344714 A1 | 11/2017 | Ballou, Jr. et al. | |
| 2018/0085251 A1 | 3/2018 | Hunter et al. | |
| 2018/0108275 A1 | 4/2018 | Newberry et al. | |
| 2018/0116871 A1 | 5/2018 | Hunter et al. | |
| 2018/0133052 A1* | 5/2018 | Huang | A61M 11/005 |
| 2018/0207030 A1* | 7/2018 | Ivri | B05B 1/086 |
| 2018/0229247 A1 | 8/2018 | Laidler | |
| 2018/0236466 A1 | 8/2018 | Laidler | |
| 2018/0297053 A1 | 10/2018 | Buckland et al. | |
| 2019/0053945 A1 | 2/2019 | Hunter et al. | |
| 2019/0074086 A1 | 3/2019 | Ballou, Jr. et al. | |
| 2019/0099071 A1 | 4/2019 | Ehrmann | |
| 2019/0224709 A1* | 7/2019 | Kelly | B05B 17/0646 |
| 2019/0314196 A1 | 10/2019 | Ivri et al. | |
| 2019/0314197 A1 | 10/2019 | Ivri et al. | |
| 2019/0314198 A1 | 10/2019 | Ivri et al. | |
| 2020/0022416 A1 | 1/2020 | Alarcon | |
| 2020/0197218 A1 | 6/2020 | Newell et al. | |
| 2020/0197220 A1 | 6/2020 | Ivri | |
| 2020/0246182 A1 | 8/2020 | Ivri | |
| 2020/0281768 A1 | 9/2020 | Quintana et al. | |
| 2020/0315842 A1 | 10/2020 | Palanker et al. | |
| 2020/0330267 A1 | 10/2020 | Li et al. | |
| 2021/0128350 A1 | 5/2021 | Ivri et al. | |
| 2021/0137732 A1 | 5/2021 | Quintana et al. | |
| 2021/0220169 A1 | 7/2021 | Ivri | |
| 2021/0322209 A1 | 10/2021 | Ivri | |
| 2022/0039998 A1 | 2/2022 | Ivri | |

(56) References Cited

U.S. PATENT DOCUMENTS

| | | | |
|---|---|---|---|
| 2022/0125631 A1 | 4/2022 | Ianchulev et al. | |
| 2022/0160542 A1 | 5/2022 | Palanker et al. | |
| 2022/0192874 A1 | 6/2022 | Ivri | |

FOREIGN PATENT DOCUMENTS

| | | | | |
|---|---|---|---|---|
| CN | 104582647 A | 4/2015 | | |
| CN | 105351426 A | 2/2016 | | |
| CN | 107530509 A | 1/2018 | | |
| EP | 0622035 A1 | 11/1994 | | |
| EP | 1493410 A | 1/2005 | | |
| JP | H08251948 A | 9/1996 | | |
| JP | 3055480 | 1/1999 | | |
| JP | 2007531577 A | 11/2007 | | |
| JP | 2013535250 A | 9/2013 | | |
| KR | 101258025 B1 | 4/2013 | | |
| KR | 1020130054352 B1 | 8/2015 | | |
| WO | 1994020875 A3 | 1/1995 | | |
| WO | 9600050 A1 | 1/1996 | | |
| WO | 2001046134 A1 | 11/2001 | | |
| WO | WO-02072169 A2 * | 9/2002 | .......... | A61M 11/005 |
| WO | 2010078428 A1 | 7/2010 | | |
| WO | 2012009706 A1 | 1/2012 | | |
| WO | 2013076682 A1 | 5/2013 | | |
| WO | 2013090459 A1 | 6/2013 | | |
| WO | 2013090468 A1 | 6/2013 | | |
| WO | 2013155201 A2 | 10/2013 | | |
| WO | 2013158967 A2 | 10/2013 | | |
| WO | 2016115050 A1 | 7/2016 | | |
| WO | 2016164830 A1 | 10/2016 | | |
| WO | 2018136618 A2 | 7/2018 | | |
| WO | 2018227190 A1 | 12/2018 | | |
| WO | 2019113483 A1 | 6/2019 | | |
| WO | 2020010116 A1 | 1/2020 | | |

OTHER PUBLICATIONS

Ali et al., "Glaucoma and Dry Eye", Ophthalmology, 2009, vol. 116, p. 1232.

Birkhoff et al., "New Devices for Dispensing Ophthalmic Treatments May Be the Key to Managing the Life Cycles of Established Products", 2010, Drug Delivery Technology, vol. 10, pp. 16-21.

Brenton, "CRUK/10/30: TRICON8—Sample collection of ovarian cancer tissues and blood for translational research from patients participating in the CR-UK/MRC ICON8 trial", 2015, online abstract.

Choi et al., "Generation of Controllable Monodispersed Sprays Using Impulse Jet and Charging Techniques", Review of Scientific Instruments, 1990, vol. 61, pp. 1689-1693.

Denion et al., "A 5-Minute Interval between Two Dilating Eye Drops Increases Their Effect", Jul. 19, 2017, Optometry and Vision Science, vol. 94, pp. 838-844.

Electronic Tutorials, "Linear Solenoid Actuator", 2016 [online]; [Retrieved on Oct. 17, 2022], Retrieved from the Internet [URL: https://www.electronics-tutorials.ws/io/io_6.html].

Elert, Glenn, "Spherical mirrors", The Physics Hypertextbook, 2021 [online]; [Retrieved on Oct. 17, 2022], Retrieved from the Internet [URL: https://physics.info/mirrors/].

Gannon, Megan, "The Best Length for Eyelashes, According to Science", Feb. 24, 2015 [online]; [Retrieved on Oct. 17, 2022], Retrieved from the Internet [URL: https://www.livescience.com/49934-optimal-length-for-eyelashes-discovered.html].

Jow et al., "Design and Optimization of Printed Spiral Coils for Efficient Transcutaneous Inductive Power Transmission", IEEE Transactions on Biomedical Circuits and Systems, 2007, vol. 1, pp. 193-202.

Kent, Christopher, "Getting Meds onto the Eye, 21st Century Style", Mar. 15, 2013 [online]; [Retrieved on Aug. 27, 2019], Retrieved from the Internet [URL: https://www.reviewofophthalmology.com/article/getting-meds-onto-the-eye-21st-century-style].

Kompella et al., "ISOPT Clinical Hot Topic Panel Discussion on Ocular Drug Delivery", 2019, J. Ocul. Pharmacol. Ther., vol. 35, pp. 457-465.

Lallemand et al., "Cyclosporine A Delivery to the Eye: A Comprehensive Review of Academic and Industrial Efforts", European Journal of Pharmaceutics and Biopharmaceutics, 2017, vol. 117, pp. 14-28.

Ianchulev et al., "Pharmacodynamic profile of mydriatic agents delivered by ocular piezo-ejection microdosing compared with conventional eyedropper", 2016, Ther. Deliv., vol. 7, pp. 751-760.

Lindblad et al., "Production of Uniform-Sized Liquid Droplets", Journal of Scientific Instruments, 1965, vol. 42, pp. 635-638.

Lux et al., "A Comparative Bioavailability Study of Three Conventional Eye Drops Versus a Single Lyophilisate", Br. J. Ophthalmol., 2003, vol. 87, pp. 436-440.

Macmillan Online Dictionary, "Stream," n.d. [online]; [Retrieved on Dec. 13, 2018]; Retrieved from the Internet [URL: https://macmillandictionary.com/dictionary/american/stream_ 1#stream_ 9].

Merriam-Webster, "Clamp," 2019 [online]; [Retrieved on Oct. 25, 2022], Retrieved from the Internet [URL: https://www.merriam-webster.com/dictionary/clamp].

Merriam-Webster, "Collimate," 2020 [online]; [Retrieved on Oct. 17, 2022], Retrieved from the Internet [URL: https://www.merriam-webster.com/dictionary/collimated].

Merriam-Webster, "Stream," n.d. [online]; [Retrieved on Dec. 13, 2018], Retrieved from the Internet [URL: https://www.merriam-webster.com/dictionary/stream].

Murube et al., "Classification of Artificial Tears, I: Composition and Properties", Advanced Experimental Medical Biology, 1998, vol. 438, pp. 693-704.

Murube et al., "Classification of Artificial Tears, II: Additives and Commercial Formulas", Advanced Experimental Medical Biology, 1998, vol. 438, pp. 705-715.

Oxford Online Dictionary, "Stream," n.d. [online]; [Retrieved on Dec. 13, 2018]; Retrieved from the Internet [URL: https://en.oxforddictionaries.com/definition/us/stream].

Pronin et al., "Teaching an Old Drug New Tricks: Agonism, Antagonism, and Biased Signaling of Pilocarpine through M3 Muscarinic Acetylcholine Receptor", 2017, Mol. Pharmacol., vol. 92, pp. 601-612.

Vocabulary.com, "Stream," n.d. [online]; [Retrieved on Dec. 13, 2018]; Retrieved from the Internet [URL: https://www.dictionary.com/stream].

* cited by examiner

302

118

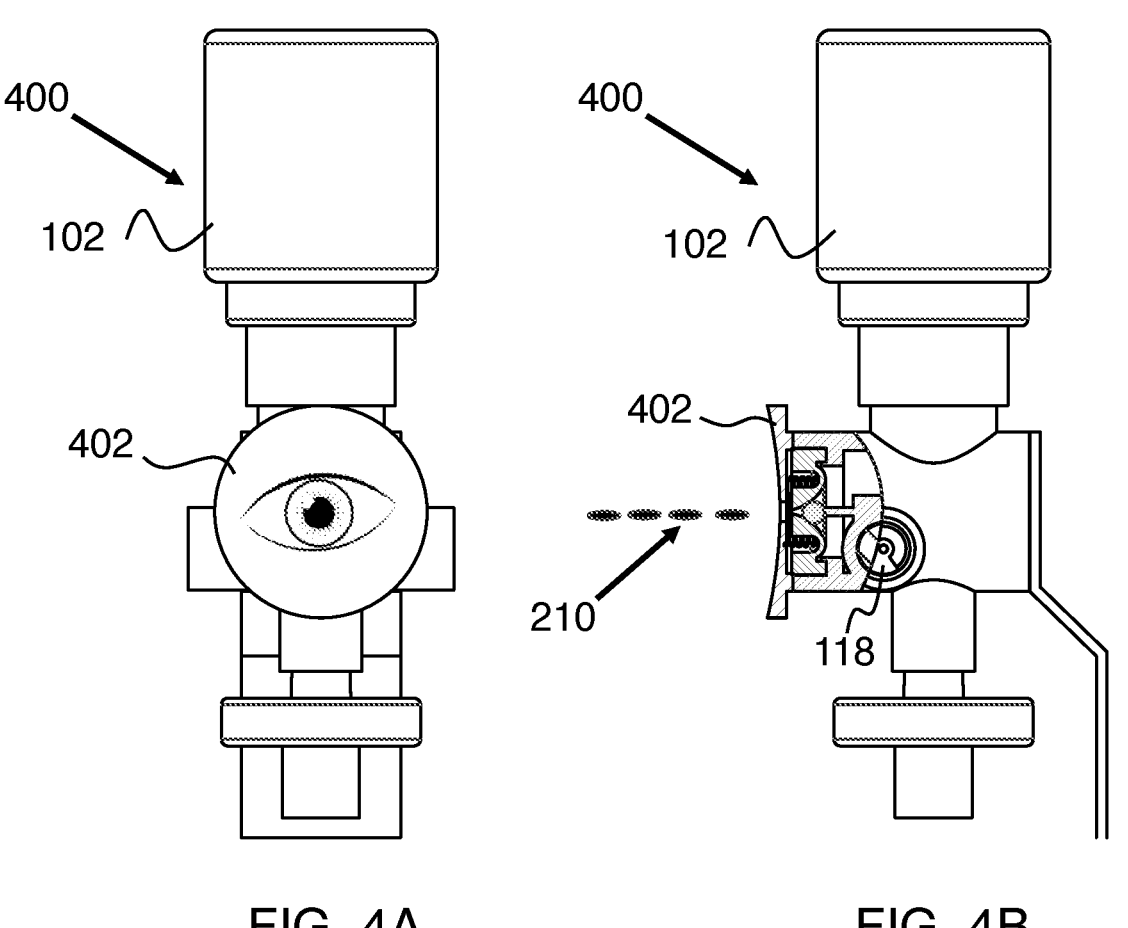
FIG. 4A                    FIG. 4B
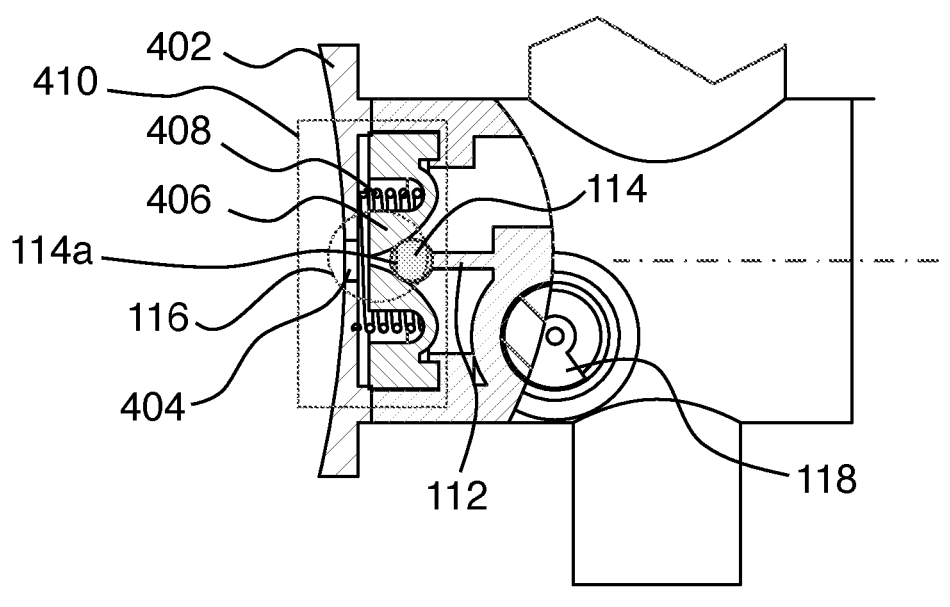
FIG. 4C

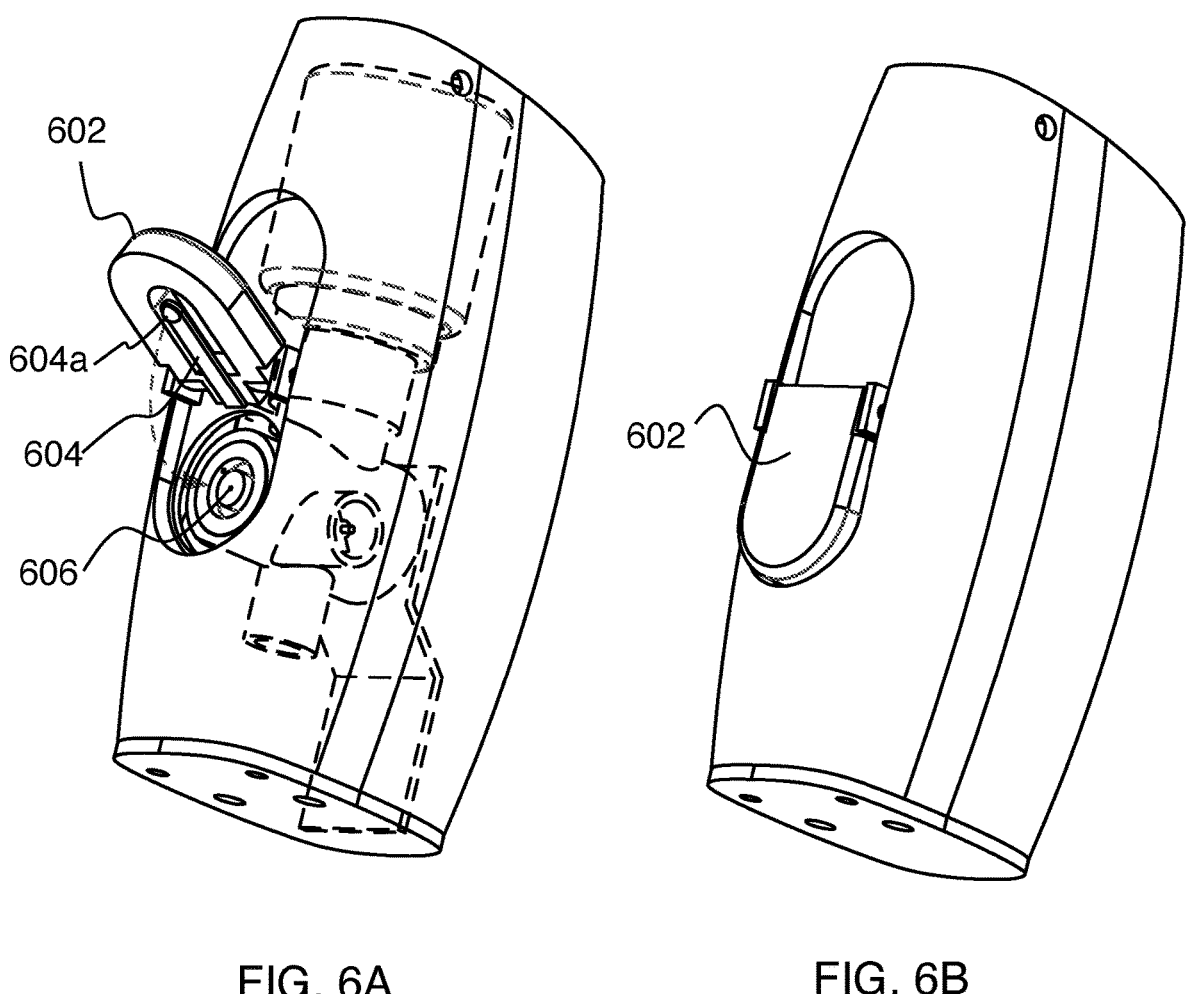
FIG. 6A                    FIG. 6B

700

702

704

706

710

708

710

712

714

HYDRODYNAMICALLY ACTUATED PRESERVATIVE FREE DISPENSING SYSTEM HAVING A COLLAPSIBLE LIQUID RESERVOIR

CROSS REFERENCE TO RELATED APPLICATIONS

This application is a continuation patent application of U.S. application Ser. No. 17/233,135, filed Apr. 16, 2021, which claims the benefit of and priority to U.S. Provisional Patent Application No. 63/011,808, filed Apr. 17, 2020, and U.S. Provisional Patent Application No. 63/166,754, filed Mar. 26, 2021, each of which are incorporated herein by reference in their entireties.

FIELD OF THE INVENTION

The present invention generally pertains to devices for dispensing fluid medicines and more particularly pertains to such devices that store and deliver ophthalmic preservative-free medicines, specifically configured to increase the ease of use and enhance patient compliance with dosing instructions for the medicine.

BACKGROUND

Ease of dispensing fluid medicines and compliance with dosing instructions are primary concerns with all patients. In particular, preservative-free dispensing bottles such as ophthalmic squeeze dispensers typically require greater actuation force due to a valve mechanism that seals the dispensing nozzle to prevent bacterial ingress and contamination. Such system requires much higher pressure to operate and hence much higher squeeze force is required. In addition, prior art dispensing bottles dispense only in an upside-down orientation which require an inconvenient head maneuver and which together with higher actuation force further increases the inconvenience.

Dispensers of the kind in question are known from the prior art, for example from U.S. Pat. Nos. 6,095,376, 9,676, 525, US 2014/0336596, US 2016/0107180, U.S. Pat. Nos. 9,238,532, 8,056,766, 8,863,998, and 10,105,720. The dispenser shown in US 2014/0336596 comprises an outlet channel which connects the liquid reservoir to the outlet opening through an outlet valve which is arranged in the outlet channel and which opens when the bottle is squeezed and pressure is generated. Such preservative-free squeeze bottles typically require about 25-28N of squeeze force (Ophthalmic Squeeze Dispenser-Drug Development and Delivery October 2017 Vol. 17 No. 7 page 40). Elderly patients, or other patients lacking enough strength and/or dexterity in their hands, often experience problems dispensing medicine from such bottles. This work provides preservative free ocular dispensing device that can be held horizontally, or in any convenient orientation while the actuation is done effortlessly by an electrical switch. This provides a cost effective solution that is consistent with standard drug packaging processes. The fluid reservoir can be made collapsible to remove the need to vent it.

SUMMARY

Multi-dose preservative-free ocular fluid delivery devices are provided. The fluid delivery device includes a fluid dispensing system and a fluid package for storing a liquid therein and supplying said liquid to the dispensing system.

The dispensing system comprises an elongated chamber which includes a check valve which defines a frontal closure to the chamber. The valve is normally closed and hermetically seals the chamber. In this work the chamber includes a vibration motor that induces oscillations to the chamber and to the fluid within. The oscillations of the chamber impart momentum to the fluid stored in the chamber which in turn imparts force that cyclically opens the valve to dispense streams or liquid droplets. Fluid is dispensed only when the motor oscillates while otherwise the valve is hermetically closed.

The check valve can include a flexible plate which includes a conical aperture that extends through its thickness, the valve can further include a stationary spherical member that engages tangentially with the inner wall of the conical aperture to create a hermetic sealed closure. The plate can be made of elastomer that has a modulus of elasticity ranging between 0.1-1.2 GPa. The circumference of the plate can be attached to the chamber by a retaining ring that engages with the chamber in an interference fit to create the hermetically sealed closure.

The conical aperture extends through the thickness of the plate such that droplets are dispensed through the smaller opening of the aperture while the larger side of the aperture is in fluid communication with the chamber.

The spherical member may include an antibacterial coating which covers the area of the spherical member that is between the tangential engagement line and the small opening of the aperture.

The vibrational motor oscillates the chamber and the fluid within the chamber. Consequently, cycles of hydrodynamic pulses are generated causing the valve to cyclically open and dispense fluid. Here this phenomenon is characterized by oscillatory interactions between the valve and the surrounding fluid. The hydrodynamic force generated by the momentum. of the fluid opens the valve and allows fluid flow through the aperture.

Fluid is dispensed only when the hydrodynamic force is sufficiently high to deform the aperture while otherwise the aperture hermetically seals the chamber. The system prevents ingress of microorganism into the chamber allowing storage of preservative free pharmaceutical. This work provides an electrically operated preservative-free dispensing system that is convenient and cost effective.

BRIEF DESCRIPTION OF THE DRAWINGS

FIG. 4A is a frontal view of an embodiment of the invention.

FIG. 4B is a side view of the embodiment of FIG. 4A.

FIG. 4C is a detail cross sectional view of the embodiment of FIG. 4A.

FIGS. 6A-B are perspective views of a device having a housing that includes a swivel cover.

DETAILED DESCRIPTION

This work describes dispensing devices and methods for delivery of preservative-free solutions or suspensions for ocular administration of ophthalmic drugs. The dispensing devices include a droplet ejecting system that is fluidly connected to an ampoule package containing a liquid to be dispensed. The droplet ejecting system includes a chamber having a check valve that defines a front closure to the chamber. The dispensing system further includes a vibration motor that oscillates the chamber and induces hydrodynamic pulses which consequently causes the valve to cyclically open and eject fluid droplets. The valve is normally closed and hermetically sealing the chamber. The valve opens exclusively in response to hydrodynamic pulses induced by the oscillation of the chamber. In this way fluid is dispensed only when the device is actuated while otherwise the aperture hermetically seals the device and prevents ingress of bacterial and microorganisms thereby allowing storage of preservative-free pharmaceutical formulation. The use of a vibration motor further enables convenient and cost effective, electronically controlled administration.

Figure 1A:
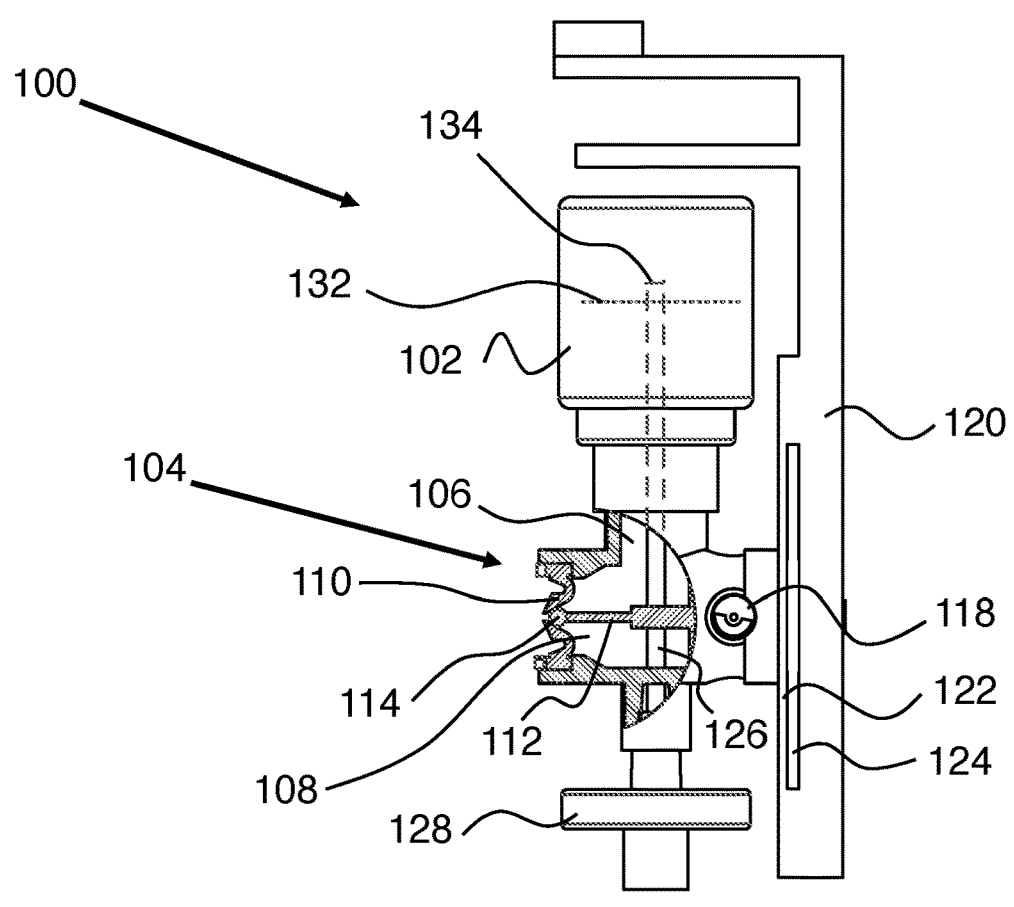
FIG. 1A is a cross sectional view of an embodiment of the invention.
Figure 1B:
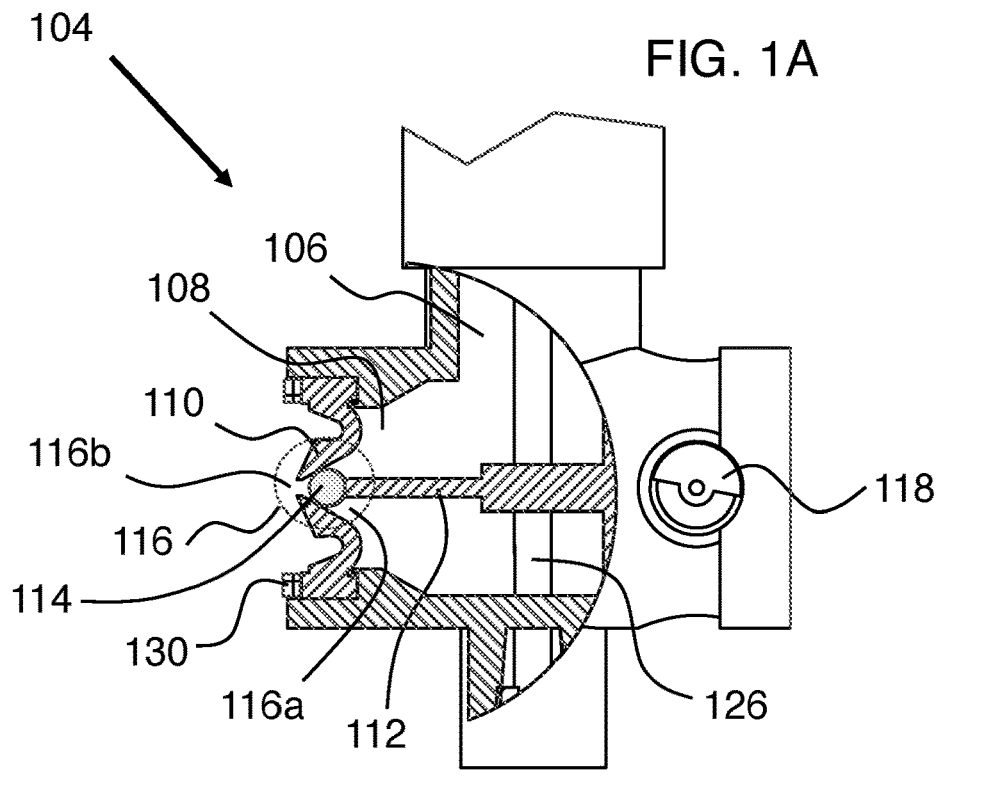
FIG. 1B is a detail cross sectional view of the embodiment of FIG. 1A.

FIG. 1A and FIG. 1B illustrate a side view and an enlarged partial section view, respectively, of a fluid delivery device 100. Delivery device 100 includes a fluid reservoir 102 and dispensing system 104 connected to each other in fluid transmission relationship though passage 106. Dispensing system 104 includes a fluid chamber 108 and also includes a check valve including aperture plate 110 which provides frontal closure to the chamber 108. Referring to FIG. 1B it can be seen that aperture plate 110 includes a conical or tapered aperture 116 (shown inside a dotted circle for clarity) that extends through its center thickness and has a large inlet opening 116*a* in fluid communication with chamber 108 and a smaller exit opening 116*b* though which fluid droplets will be dispensed. Aperture plate 110 can be made of a flexible elastomer such as silicone rubber, VersaFlex, manufactured by VersaFlex Incorporated Kansas City, Kans. USA. Other elastomers with Young modulus of elasticity value between 0.5 GPa to 2 GPa can also be used. Dispensing system 104 further includes a stationary spherical member 114 that tangentially engages in pressure transmission relationship with the inlet opening 116*a* of the conical aperture providing hermetically sealed closure. In a preferred embodiment spherical member 114 is made of high density polyethylene (HDPE) that is harder than silicone thereby creating a tight closure as it engages with the softer aperture plate 110. Spherical member 114 preferably engages in pressure transmission relationship with the conical aperture 116*a* with a preload force of between 0.01N and 0.05N. The combination of aperture plate 110 and spherical member 114 provides a check valve as described above. Spherical member 114 is supported by pin member 112. Member 114 can have a shape other than spherical, since any shape capable of forming a good seal with aperture plate 110 can be used.

Aperture plate 110 can be retained to dispensing system 104 by a retaining ring 130, thereby creating a hermetically sealed closure.

Dispensing system 100 includes a venting tube 126 that is configured to equalize the pressure inside container 102 as the fluid is dispensed from the device. The opening 134 of venting tube 126 is extended above the fluid level 132 at any orientation that the device is held. Vent tube 126 can be connected via a 0.22 micron filter 128 to assure that the air that enters the device is sterile.

Dispensing system 100 further includes a vibration motor configured to oscillate chamber 108 and the fluid within the chamber. Here this motor is schematically shown as eccentric mechanical load 118 which vibrates the assembly as described when it is rotated by the motor (motor not shown in FIGS. 1A-B, but described below in connection with FIG. 3).

Figures 1C, 2A, 2B:
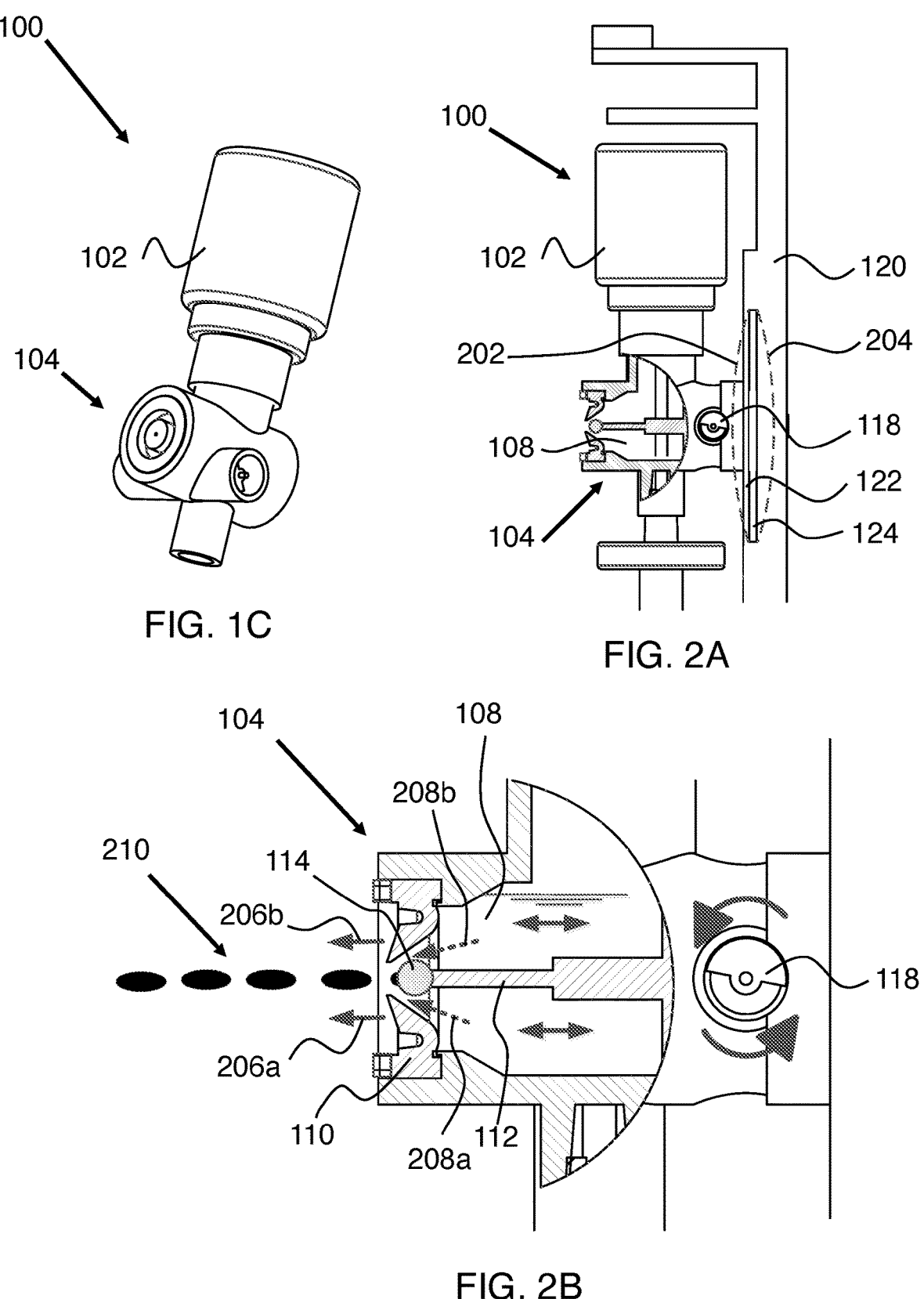
FIG. 1C is a 3D view of the embodiment of FIGS. 1A-B.
FIG. 2A is a side view and partial cross section view of an embodiment of the invention in operation.
FIG. 2B is a detail cross section view of the example of FIG. 2A.

FIG. 1C is a 3D view of the embodiment of FIGS. 1A-B.

FIGS. 2A-B illustrate the response of the dispensing system 104 to oscillations. Vibrations of the motor induce oscillation to the body of dispensing system 104 which in turn generates fluid momentum within the chamber due to the dynamical interaction of the fluid with the solid structure of chamber 108. This phenomenon is often referred to as Solid-Fluid-Interaction (SFI). The momentum of the moving fluid exerts force that flexes the aperture plate 110 outwardly in the direction indicated by arrows 206*a* and 206*b* causing the aperture plate 110 to disengage from spherical member 114 thereby opening a fluid flow passage as indicated by the arrows 208*a* and 208*b* and ejection of fluid droplets 210.

Dispensing device 100 is supported by a flexible beam 122 or other structural embodiments which allows it to oscillate freely, as schematically shown by motion excursions 202 and 204. Preferably the spring constant of the beam 122 is 0.05 N/mm to 0.5 N/mm. For example, beam 122 can be formed by fabricating a slot 124 in support structure 120 such that the resulting beam 122 has a thickness suitable for providing a spring constant as recited above.

Figure 3:
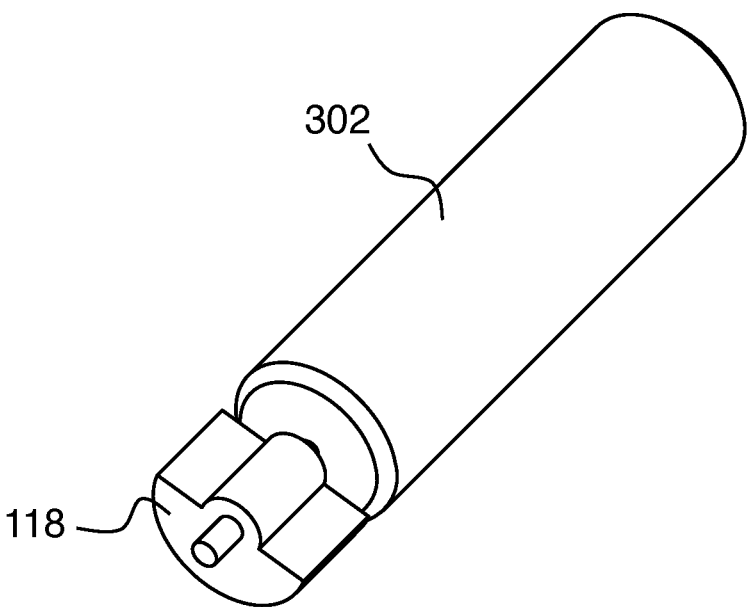
FIG. 3 illustrates a perspective view of a vibration motor as used in embodiments of the invention.

FIG. 3 illustrates an exemplary vibrational motor 302. The DC Motor 302 of this example has a cylindrical body with a diameter of 4 mm and total length of 17 mm. An eccentric flywheel 118 is attached to the motor shaft. The flywheel has a mass of 1.7 grams with a center of mass about 0.7 mm from the center of rotation. The motor receives 4.5-12 VDC and rotates at 6000-12000 RPM generating centrifugal force of 0.3N at a rotation speed of 8000 RPM. Other DC motors that generate centrifugal force of 0.1-1N and rotation speed of 1000-50000 RPM can be used. The motor can be controlled by a timer circuit which is set to provide an ON time as required to deliver a dose of 8-12 micro-liter. The actuation ON time is 60-200 ms depending on the rheology of the fluid in use. A timer circuit which incorporates a 555 timer IC or a microprocessor-based timer with a 12 volt battery such as A23 alkaline battery may be used.

FIGS. 4A-C illustrate an alternative preferred embodiment of dispensing system 400. FIG. 4A illustrates a frontal view and FIG. 4B illustrates a side view of dispensing system 400. Dispensing system 400 includes a concave mirror 402 which assists in aligning device 400 and fluid stream 210 to the eye of the user. In use, dispensing device 400 is positioned in front of the eye such that the image of the eye appears sharply and in the center of mirror to the user. At this point the device is properly positioned in term of the distance of the eye from the nozzle 404 and its angular orientation relative to the eye. Upon actuation, stream 210 will be deposited precisely on the corneal surface of the eye. Device 400 preferably includes a 0.22 micron air filter configured to filter the vented air that flows into device 400, as in the previous example.

Device 400 includes a check valve having an aperture plate 406 with a conical aperture 116 that extends through its thickness. The check valve further includes a spherical member 114 that tangentially engages with the inlet opening of the conical aperture 116. In this example, the check valve also includes a compression spring 408 configured to force aperture plate 406 against spherical member 114. In this way a tight seal is created along the engagement line 114a, thus creating a tight and hermetic closure.

Spherical member 114 can be partially covered with an antimicrobial coating, specifically in the area of spherical member 114 that is not in contact with fluid in the chamber. The coated area thus extends between the engagement line 114a and the outlet of the conical aperture (i.e., to the left of 114a on FIG. 4C)). Examples of antimicrobial coatings include silver in metallic form, silver alloy or a non-metallic material that contains silver including salts of silver chloride and silver sulfadiazine. Other optional material includes biguanide derivatives, chlorohexidine diacetate and chlorohexidine digluconate.

Figures 5A, 5B:
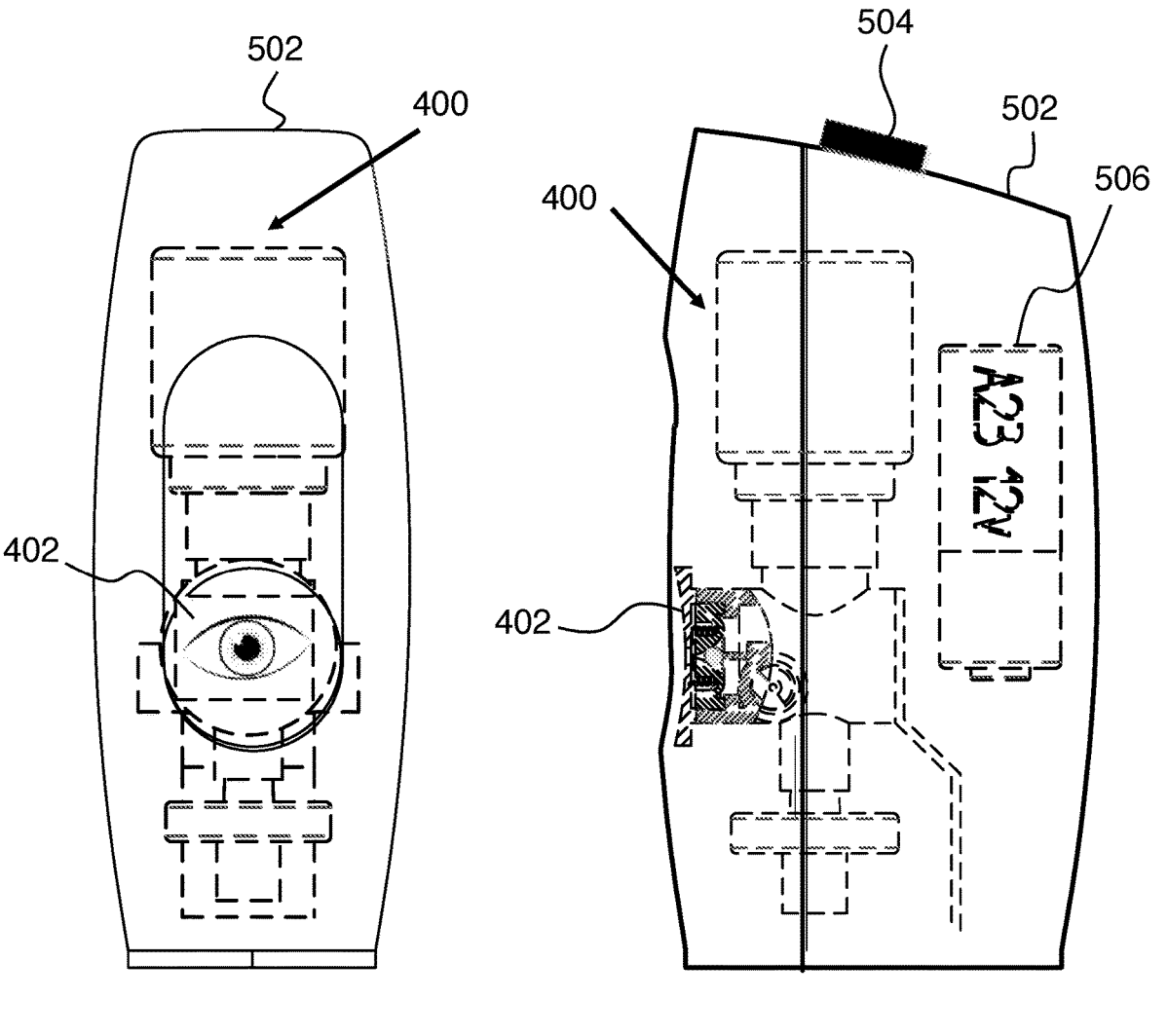
FIG. 5A is a frontal view of an exemplary device enclosed in a housing.
FIG. 5B is a side view of the example of FIG. 5A.

FIGS. 5A-B illustrate frontal and side views, respectively, of a dispensing device 400 packaged in a housing 502. Housing 502 provides a convenient enclosure to the dispensing system 400 that was described in relation in FIGS. 4A-C and is shown with dashed lines here. Housing 502 includes an electrical circuit (not shown) and a 12-volt battery (e.g., type A23) 506. The circuit controls the dispensing period such that a dose of 8-12 microliter is delivered to the ocular surface of the eye. Momentary switch 504 can be used to activate the device 400 such that a stream of droplets is ejected from the aperture as described earlier. FIGS. 5A-B also illustrate the mirror 402 which is visible on the front side of the device. Such a housing can also be used for a dispensing device 100 as described above.

FIGS. 6A-B illustrate some preferred features of housings that can be used with embodiments such as device 100 and device 400 as described above. In this example, the housing includes a swivel cover 602 that covers dispensing nozzle 606 during periods of non-use. Swivel cover 602 provides a means to prevent bacterial contamination on the external areas where a residual fluid may be left following each use. Such residual fluid may contaminate subsequent stream as it is dispensed through the nozzle. Swivel cover 602 preferably includes a flexible member 604 that includes a surface 604a that is covered with antimicrobial coating. Surface 604a engages with the outlet opening of nozzle 606 when the swivel cover 602 is closed as illustrated in FIG. 6B. In this way antipathogen action is achieved. Alternatively, organic dyes with antiseptic action may also be used. For example, toluidine blue, methylene blue, gentian violet and acridine and related active substances such as acridine orange and acridine yellow as well as ethacridine lactate. Germicidal polymers such as polyhexanide are also possible. Materials that contain additives which contain metal-organic substances with an ionizing effect can also be used. Such additives are available from SteriOne GmbH Berlin, Germany. Examples of antimicrobial coatings that can be used on surface 604a include silver in metallic form, silver alloy or a non-metallic material that contains silver including salt of silver chloride and silver sulfadiazine. Other optional material includes biguanide derivatives, chlorohexidine diacetate and chlorohexidine digluconate.

Figures 7A, 7B:
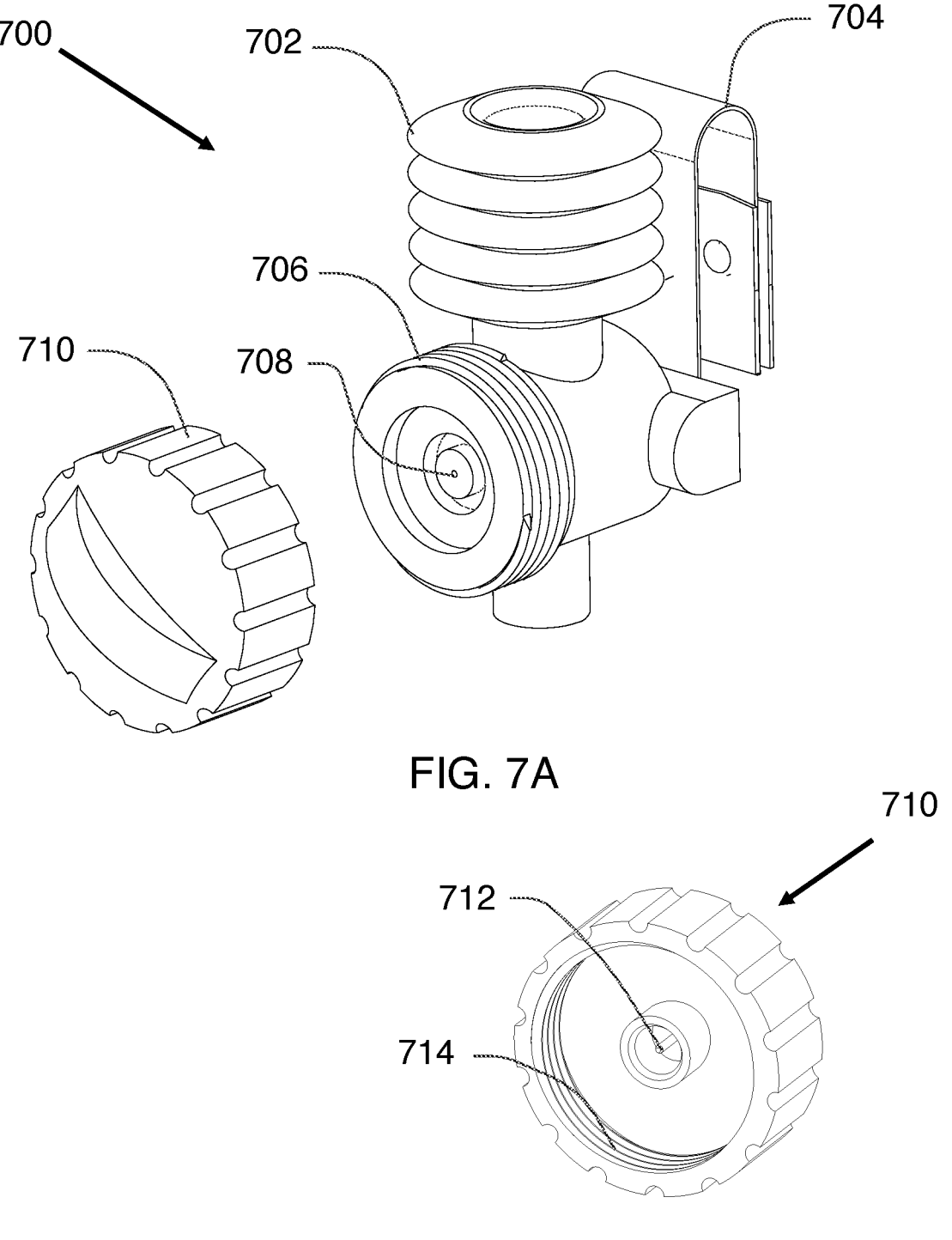
FIGS. 7A-B shown another embodiment of the invention.

FIGS. 7A-B illustrate a dispensing system 700 utilizing an alternative fluid reservoir 702 configured to eliminate the need for venting and air filtering as previously described in relation to other embodiments. Dispensing system 700 includes a collapsible fluid chamber (e.g., a bellows) 702 containing ophthalmic solution to be dispensed. When fluid is dispensed the internal pressure inside the bellows 702 is gradually reduced which results in axial deformation of bellows 702 which in turn equalizes the pressure inside bellows 702 with the atmospheric pressure. In this way fluid inside the bellows 702 does not need to be vented to the atmosphere and further may not have to be in contact with air and particularly oxygen. Such a system is particularly advantageous for ophthalmic fluids that are sensitive to oxidation. Dispensing system 700 further includes cap 710 that seals off the dispensing nozzle during non-use period. FIG. 7B illustrates a frontal view of cap 710. It can be seen that cap 710 has an internal thread 714 that engages with the external thread 706. Cap 710 further includes a central pin 712 that is configured to seal off dispensing aperture 708 during periods of non-use. Apparatus 700 includes a flexible mount 704 to permit a vibration motor to vibrate the apparatus to eject liquid as described above.

Figure 8A:
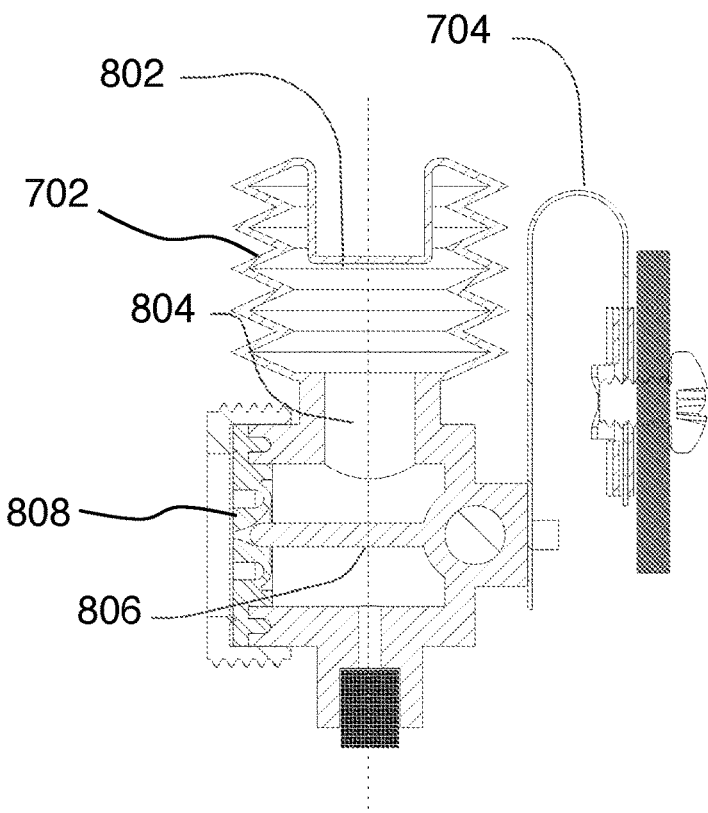
FIGS. 8A-B are cross section views of the example of FIGS. 7A-B.
Figure 8B:
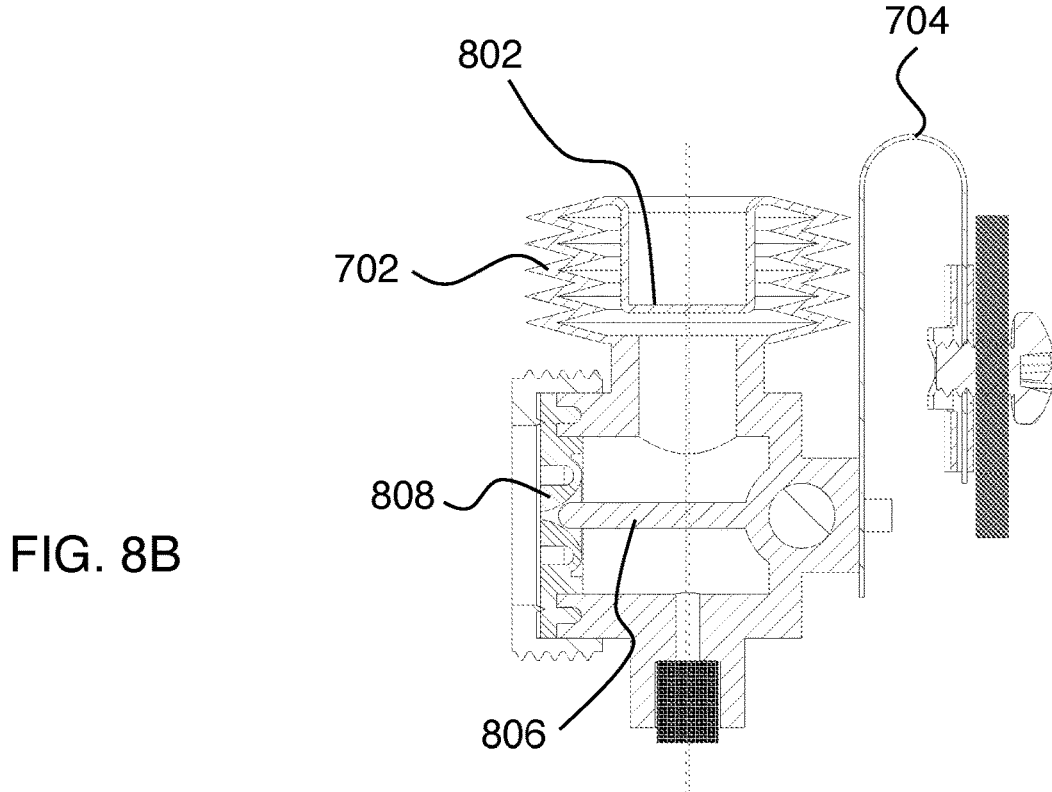

FIG. 8A illustrates a cross-sectional view of the dispensing system of this example when bellows 702 is filled with fluid while FIG. 8B shows the bellows 702 in a collapsed or nearly empty state. It can be seen that the open end of bellows 702 is connected to the dispensing chamber 804. Preferably the sealed end of the bellows is recessed inwardly toward the bellows forming a cup-shaped indentation 802 as shown. In this way the unused volume that is left in bellows 702 once it is fully collapsed is minimized, as shown on FIG. 8B. Here stationary member 806 and flexible aperture plate 808 form a check value that operates as described above when the apparatus is vibrated by a vibration motor.

What is claimed is:

1. A method for delivering fluid to a targeted site, the method comprising:

using an actuator to oscillate a fluid containing chamber in fluid communication with a reservoir to generate fluid momentum in the chamber such that the fluid deforms an aperture of the chamber, the actuator comprising a vibration motor having an eccentric mechanical load relative to an axis of rotation of the vibration motor, wherein the actuator is configured to induce vibrations to a housing to generate the fluid momentum;

allowing a pin positioned within the chamber and in fluid-tight engagement with the aperture of the chamber to disengage from one another in the presence of the generated fluid momentum so that the fluid can be ejected through the aperture to the targeted site; and collapsing the reservoir as the fluid is ejected to equalize pressure within the reservoir with atmospheric pressure.

2. The method of claim 1, wherein the fluid is an ophthalmic fluid sensitive to oxidation.

3. The method of claim 1, wherein, in the using step, the reservoir is a bellows.

4. The method of claim 3, wherein, in the collapsing step, the bellows is axially deformed to equalize the pressure therein with the atmospheric pressure outside the bellows.

5. The method of claim 1, wherein, in the collapsing step, the pressure within the reservoir is equalized without introducing air into the reservoir.

6. The method of claim 1, wherein, in the collapsing step, the reservoir is attached to the chamber at a first end and a second end, opposite the first end, is recessed inward as the reservoir is collapsed.

7. The method of claim 6, wherein the second end forms a cup-shaped indentation.

8. The method of claim 1, further comprising:

reengaging the aperture with the pin to seal the aperture after the fluid is delivered.

9. The method of claim 8, wherein the reengaging step further comprises preventing an ingress of bacteria or contaminants as a result of an engagement between the aperture and the pm.

10. The method of claim 1, further comprising:

biasing the aperture against the pin via a compression spring.

11. An apparatus for delivering a fluid to a targeted site, the apparatus comprising:

a fluid containing chamber having a deformable aperture through which the fluid can be selectively dispensed;

an actuator engaging the chamber to generate fluid momentum therein to open the deformable aperture for fluid ejection therethrough, the actuator comprising a vibration motor having an eccentric mechanical load relative to an axis of rotation of the vibration motor, wherein the actuator is configured to induce vibrations to a housing to generate fluid momentum; and a reservoir in fluid communication with the chamber and collapsible to equalize pressure within the reservoir with atmospheric pressure as the fluid is being ejected.

12. The apparatus of claim 11, wherein the fluid is an ophthalmic fluid sensitive to oxidation.

13. The apparatus of claim 11, wherein the reservoir is a bellows.

14. The apparatus of claim 13, wherein the bellows is axially deformed to equalize the pressure therein with the atmosphere.

15. The apparatus of claim 11, wherein the pressure within the reservoir is equalized without introducing air into the reservoir.

16. The apparatus of claim 11, wherein the reservoir is attached to the chamber at a first end and a second end, opposite the first end, is recessed inward as the reservoir is collapsed to minimize unused fluid within the reservoir.

17. The apparatus of claim 16, wherein the second end forms a cup-shaped indentation.

18. The apparatus of claim 12, further comprising a pin member engaging the aperture such that the aperture, as a result of the fluid momentum, is disengaged from the pin member.

* * * * *